(12) United States Patent
Krishnamoorthy et al.

(10) Patent No.: US 11,754,527 B2
(45) Date of Patent: Sep. 12, 2023

(54) AFFINITY SENSOR, IN PARTICULAR QCM SENSOR

(71) Applicant: LUXEMBOURG INSTITUTE OF SCIENCE AND TECHNOLOGY (LIST), Esch-sur-Alzette (LU)

(72) Inventors: Sivashankar Krishnamoorthy, Esch-sur-Alzette (LU); Matteo Beggiato, Esch-sur-Alzette (LU)

(73) Assignee: LUXEMBOURG INSTITUTE OF SCIENCE AND TECHNOLOGY (LIST), Eschsur Alzette (LU)

( * ) Notice: Subject to any disclaimer, the term of this patent is extended or adjusted under 35 U.S.C. 154(b) by 0 days.

(21) Appl. No.: 17/636,084

(22) PCT Filed: Aug. 18, 2020

(86) PCT No.: PCT/EP2020/073106
§ 371 (c)(1),
(2) Date: Feb. 17, 2022

(87) PCT Pub. No.: WO2021/032745
PCT Pub. Date: Feb. 25, 2021

(65) Prior Publication Data
US 2022/0291172 A1    Sep. 15, 2022

(30) Foreign Application Priority Data
Aug. 19, 2019   (LU) ........................ 101353

(51) Int. Cl.
*G01N 29/02*   (2006.01)
*B82Y 5/00*    (2011.01)
*B82Y 15/00*   (2011.01)

(52) U.S. Cl.
CPC .............. *G01N 29/022* (2013.01); *B82Y 5/00* (2013.01); *B82Y 15/00* (2013.01); *G01N 2291/0256* (2013.01)

(58) Field of Classification Search
CPC ......... G01N 29/022; G01N 2291/0256; G01N 29/222; G01N 2291/0426; B82Y 5/00; B82Y 15/00
See application file for complete search history.

(56) References Cited

U.S. PATENT DOCUMENTS

| 2003/0006446 | A1  | 4/2003  | Mirkin |
| 2003/0068446 | A1* | 4/2003  | Mirkin ................. B01J 19/0046 |
|              |     |         | 506/40 |
| 2004/0235198 | A1* | 11/2004 | Marx ............... G01N 33/54373 |
|              |     |         | 436/63 |
| 2010/0151791 | A1  | 6/2010  | Himmelhaus |

(Continued)

FOREIGN PATENT DOCUMENTS

| WO | WO-2005090973 A1 * | 9/2005 | ............. B82Y 15/00 |
| WO | WO-2021032745 A1 * | 2/2021 | ........... G01N 29/022 |

OTHER PUBLICATIONS

International Search Report for corresponding application PCT/EP2020/073106 filed Aug. 18, 2020; dated Oct. 29, 2020.

(Continued)

*Primary Examiner* — Francis C Gray
(74) *Attorney, Agent, or Firm* — CANTOR COLBURN LLP

(57) ABSTRACT

An aspect of the invention pertains to an affinity biosensor for sensing an analyte (a biomolecule) in a fluid, comprising an interface for contacting the fluid and adsorption of the analyte. The interface comprises a binary pattern of nanoscale regions having affinity for the analyte and a passivated region. The nanoscale regions are isolated from one another by the passivated region in such a way that adsorption of the analyte on the interface is confined to the nanoscale regions. The nanoscale regions have diameters comprised in the range from 5 to 200 nm. The nanoscale regions have together a surface area amounting to at least 15% of the surface area of the interface. A further aspect of the invention relates to a method of using such a sensor.

22 Claims, 10 Drawing Sheets

(56) References Cited

U.S. PATENT DOCUMENTS

2010/0256016 A1     10/2010  Blair
2017/0184584 A1*    6/2017   Lin ................. G01N 33/54353

OTHER PUBLICATIONS

Written Opinion of the International Searching Authority for corresponding application PCT/EP2020/073106 filed Aug. 18, 2020; dated Oct. 29, 2020.
A. Valsesia, "Protein Nanopatterns for Improved Immunodetection Sensitivity", Anal. Chem. 2008, 80, 7336-7340.
Brigitte Stadler, "Nanopatterning of Gold Colloids for Label-free biosensing", Nanotechnology 18 (2007) 155306.
Fung Ling Yap, "Nanoparticle Cluster Arrays for High-Performance SERS through Directed Self-Assembly on Flat Substrates and on Optical Fibers", vol. 6, No. 3 2012, 2056-2070.
Marco Riedel, "Protein adsorption and monocyte activation on germanium nanopyramids", Biomaterials 22 (2001) 2307-2316.
Patricia Lisboa, "Thiolated polyethylene oxide as a non-fouling element for nano-patterned bio-devices", Applied Surface Science 253, 2007, 4796-4804.
Sanghamitra Dinda, "Gold nanoparticles adsorption study onto periodic block copolymer using quartz crystal microbalance", Material Letter (2015) 118-121.
Sivashankar Krishnamoorthy, "Confinement-Induced Enhancement of Antigen-Antibody Interactions within Bianary Nanopatterns to Achieve Highr Efficiency of On-Chip Immunosensors", Adv. Mater 2008, 20, 2782-2788.

* cited by examiner

AFFINITY SENSOR, IN PARTICULAR QCM SENSOR

FIELD OF THE INVENTION

The invention generally relates to affinity sensors, in particular quartz crystal microbalance (QCM) sensors. A further aspect of the invention relates to a method of sensing an analyte in a fluid using such a sensor.

BACKGROUND OF THE INVENTION

Confinement of adsorption processes to tiny spaces of the order of few multiples of adsorbate dimensions is encountered in sensing devices employing nanoscale components.

Spatial confinement of adsorption events is a consequence of device footprint miniaturization. The outcome of the adsorption events is of interest for a broad range of applications, including nanosensors, cell-substrate interactions, antibacterial surfaces, adsorption within pores, etc.

Different techniques have been used for nanopatterning of biological receptors, including colloidal lithography, block copolymer derived nanoparticle arrays, porous alumina, electron beam or nanoimprint lithography, and AFM (atomic force microscope) based methods. However, the impact of adsorbing areas at the nanoscale on the outcome of adsorption, namely, the density of adsorbate or the kinetics of adsorption has not been investigated.

Colloidal lithography has been used previously to generate binary nanopatterns for selective adsorption of biomolecules to sub-micron patches on surface. The paper by Krishnamoorthy, S.; Himmelhaus, M., "Confinement-Induced Enhancement of Antigen-Antibody Interactions within Binary Nanopatterns to Achieve Higher Efficiency of on-Chip Immunosensors," *Adv. Mater.* 2008, 20 (14), 2782-2788, found such patterns to increase sensitivity of immunoassays, and attributed this to enhanced orientation of the capture antibody on nanopatterns. However, the investigation does not address the impact of such confinement on the surface concentration of receptors or response times of the assay.

Similarly, the paper by Agheli, H.; Malmström, J.; Larsson, E. M.; Textor, M.; Sutherland, D. S., "Large Area Protein Nanopatterning for Biological Applications," *Nano Lett.* 2006, 6 (6), 1165-1171 discloses realization of an array of nanopatches using colloidal lithography in the 100 nm range. The authors of that paper were able to quantify the impact of nanopatterns for monoclonal antibodies bound to proteins, opening to the possibility that binding sites on protein may be more available on nanopatterns than on homogeneous surfaces.

Valsesia, A.; Mannelli, I.; Colpo, P.; Bretagnol, F.; Rossi, F., "Protein Nanopatterns for Improved Immunodetection Sensitivity," *Anal. Chem.* 2008, 80 (19), 7336-7340 reports production of a binary pattern of COOH spots in a PEO matrix with different template periodicity and spots diameter. By comparing the surface with Ab-IgG at different concentration the authors proved that the limit of detection was effectively shifted towards lower concentration when nanopatterns were used. However, since the variables changed at once for all the experiments, the impact of the change of the lattice constant and of the spot diameter could not be determined. With their work, they proved that the activity of the IgG was increased by checking it with anti-IgG and that the recognition capability was enhanced due to the presence of nanopatterns.

In the paper by Kim, P.; Kim, D. H.; Kim, B.; Choi, S. K.; Lee, S. H.; Khademhosseini, A.; Langer, R.; Suh, K. Y., "Fabrication of Nanostructures of Polyethylene Glycol for Applications to Protein Adsorption and Cell Adhesion," *Nanotechnology* 2005, 16 (10), 2420-2426, fluorescence analysis was used to map the impact of nanopatterned PEG surfaces on testing protein adsorption, when compared to homogeneous PEG surface. It also addressed the increased in fluorescence to the increased surface area without, though, excluding the possibility of other effects related to surface energy.

While aiming at improving the cell behavior on germanium nanopyramids to reach less inflammatory reactions through a protein adsorption study, Riedel, M.; Müller, B.; Wintermantel, E., in "Protein Adsorption and Monocyte Activation on Germanium Nanopyramids," *Biomaterials* 2001, 22 (16), 2307-2316, came to a point where the density of the nanopyramids directly influences the available active sites for the proteins themselves. The results were compared with the surface area increase. The increase of 2.5-3 times was much beyond the 7% increase in surface area. Furthermore, while the density was scaling up, the activity of the bovine-gamma-globulin was reducing until it was totally inactive at the maximum density available. The work of Riedel et al. was taking advantage of a material contrast between the background and the patterns which is not normally shown in other work and that might explain the higher adsorption coverage since germanium and silicon might have a different mass uptake or adsorption kinetic when exposed to proteins or, as suggested by the paper, the adsorption might have taken place on top of the pyramids in greater quantity than on the background.

The paper by Dolatshahi-Pirouz, A.; Rechendorff, K.; Hovgaard, M. B.; Foss, M.; Chevallier, J.; Besenbacher, F., "Bovine Serum Albumin Adsorption on Nano-Rough Platinum Surfaces Studied by QCM-D," *Colloids Surfaces B Biointerfaces* 2008, 66 (1), 53-59, studied the influence of a stochastically nano-rough platinum surface on bovine serum albumin adsorption as compared to a flat surface. By comparing the normalized mass uptake, the authors noticed an increment which could not be indicative of the increase in surface area only. This increment was attributed to a better steric arrangement of the adsorbate on the surface, resulting to an increase in mass uptake of the order of 30-35%.

In the majority of the works presented above, one was able to identify a 3$^{rd}$ party influence coming into play when the protein adsorption was taking place and that was not traceable to an increase in surface area only. Certain scenarios can be considered as a fouling nanopattern on a fouling background, since the contributions of the background were still clearly contributing to the overall solute adsorption as well as to the available surface. On the other hand, the works of Valsesia et al. and Krishnamoorthy et al. proposed adsorption of a solute on specific areas on the surface (fouling patches in anti-fouling background approach).

SUMMARY OF THE INVENTION

There is no certainty in the prior art on how the nanopatterns affect the adsorption of a solute. While some authors proved an enhancement in solute adsorption on nanopatterns that went beyond what one would have expected due to the surface area, no situation has been reported where only sites, which are few orders of magnitude larger than the adsorbate species, were available for adsorption.

One important challenge in this context is to confine adsorption events within pre-determined areas down to molecular dimension. In addition, these areas need to be available in high enough density over relatively large surfaces (e.g. several square millimeters) to enable analysis with high signal-to-noise ratios and/or to cater to techniques with large measurement footprints, such as QCM, SPR (surface plasmon resonance) and ellipsometry.

A first aspect of the invention pertains to an affinity sensor, in particular an affinity biosensor, for sensing an analyte in a fluid (a liquid or a gas), comprising an interface for contacting the fluid and adsorption of the analyte. The interface comprises a binary pattern of nanoscale regions having affinity for the analyte and a passivated region. The nanoscale regions are isolated from one another by the passivated region in such a way that adsorption of the analyte on the interface is confined to the nanoscale regions. The nanoscale regions have diameters comprised in the range from 5 to 200 nm. Furthermore, the nanoscale regions have together a surface area amounting to at least 15% of the surface area of the interface.

As used herein, the term "affinity sensor" designates a sensor relying on the binding of the analyte (species to be detected qualitatively or, preferably, quantitatively) to a selective component without, however, consuming the analyte in a chemical reaction. In the context of the present disclosure, the affinity sensor is also a biosensor (affinity biosensor), wherein the selective component comprises a sensitive biological element, e.g. an antibody or receptor that the analyte binds to. The analyte preferably includes a biomolecule, e.g. a protein, a carbohydrate, a lipid, a nucleic acid. Such biomolecule could be attached to some other entity (another molecule or biomolecule, a nanoparticle, or the like).

Using an affinity sensor according to the first aspect of the invention, the inventor were able to demonstrate that the confinement of adsorbate onto nanoscale regions on surface can significantly affect the receptor densities and the kinetics of adsorption. They further noted the effect to be qualitatively similar for biomolecules, or synthetic nanoscale objects of comparable dimensions.

In the context of the present document, the term "diameter" means the smallest distance that can be formed between two opposite parallel planes tangent to the convex hull of the object under consideration. The measurement of diameters may be made by SEM and/or AFM, using direct and/or indirect measurements. If direct diameter measurements with SEM turn out to be difficult because the boundaries of the objects under consideration are not neat (in case of a highly charging surface), the measurements can be made using AFM or indirect measurement by SEM. It is known that AFM suffers from tip convolution effects, which affect the lateral resolution. Nevertheless, these effects can be corrected to some extent by taking the tip specifications into account. Feature diameters can also be measured indirectly by SEM. According to this technique, conducting (e.g. metal) nanoparticles of known diameter are adsorbed on the object under consideration in order to improve conductivity and resolution. The diameter of the object under consideration can then be determined using the double nanoparticle diameter as the maximum possible deviation.

It is worthwhile noting that the sensor interface can be flat or have a three-dimensional (3D) surface. The same is true for the nanoscale regions. Accordingly, to calculate the ratio $A_{nano}/A_{interface}$ (fill factor), where $A_{nano}$ is the surface area of the nanoscale regions taken together and $A_{interface}$ is the total surface area of the interface (including the nanoscale regions and the passivated region), the 3D shape of the surfaces has to be taken into account. Preferably, the nanoscale regions together have a surface area amounting to at least 20%, more preferably to at least 25% and most preferably to at least 30%, of the surface area of the interface. To the best knowledge of the inventors, nanopatterned affinity sensors with a fill factor high as 15% have not been reported in the literature. It will be appreciated that the high fill factor implies that the enhancement of the adsorption in the nanoscale regions may result in overall adsorbed masses comparable or even higher than those that can be obtained with un-patterned sensors, despite of the lesser surface area available for adsorption.

The nanoscale regions may comprise nanodomes (nanoscale domes or pillars) protruding from the passivated region. Alternatively or additionally, the nanoscale regions could comprise nanopores (nanoscale pores) recessed from the passivated region and/or nanoscale regions that are flush with the passivated region. Experiments have shown that an enhancement of the adsorption densities can be observed with relatively flat nanodomes making up to fill factors above 60%. Higher fill factors (e.g. 95%) can be achieved by increasing the height of the nanoscale regions, so as to form nanoscale pillars.

If the affinity sensor has nanodomes, these preferably comprise a silica core. Nevertheless, alternatives to silica exist and are not excluded. Possible alternatives include metals (in particular: gold) and polymers.

The nanoscale regions preferably have a surface functionalization that is selective for the analyte. In this context, "selective functionalization" means interaction between a species in solution and the surface which is mediated by a specific receptor (e.g. biotin/avidin interaction or antigen/antibody interaction).

The nanoscale regions preferably have an average diameter comprised in the range from 40 to 170 nm.

The nanoscale regions are preferably arranged in a hexagonal lattice (also called "triangular lattice"), where each lattice point has 6 nearest neighbours spaced by angles of about 60° and located at about the same distance from the lattice point under consideration. It should be noted that the hexagonal lattice may, in practice, have irregularities or defects. Apart from isolated defects, the defects may divide the lattice structure into grains, the grains themselves having a substantially regular configuration. Preferably, the lattice has an average grain diameter amounting to at least 5, preferably at least 6, 7, 8, 9 or 10 times the pitch of the lattice.

Preferably, when the nanoscale regions form a hexagonal lattice, the average centre-to-centre distance between nearest-neighbour nanoscale regions amounts to between 1.3 and 5 times (more preferably, to between 1.4 and 4.7 times) the average diameter of the nanoscale regions. Preferably, the centre-to-centre distances exhibit a standard deviation less than 20% (more preferably: less than 15%) of the average centre-to-centre distance.

The passivated region may comprise an anti-fouling layer. For instance, the passivated region could comprise a layer of protein-resistant polyethylene glycol moieties.

In a further aspect, the invention relates to a quartz crystal microbalance chip implemented as an affinity sensor as described herein, wherein the interface corresponds to the QCM surface for taking up mass. The QCM chip comprises a substrate contacted by electrodes for inducing therein shear deformations through the piezoelectric effect. Preferably, the QCM chip is implemented in a QCM with dissipation monitoring (QCM-D).

According to a preferred embodiment, the QCM chip implemented as an affinity biosensor, wherein:
- the nanoscale regions comprise nanodomes protruding from said passivated region;
- the nanoscale regions have a surface functionalization selective for the analyte, whereas the passivated region comprises an anti-fouling layer, e.g. a layer of protein-resistant polyethylene moieties;
- the nanoscale regions have an average diameter comprised in the range from 40 to 170 nm;
- the nanoscale regions are arranged in a hexagonal lattice; and
- the average centre-to-centre distance between nearest-neighbour nanoscale regions amounts to between 1.5 and 5 times the average diameter of the nanoscale regions According to yet a further aspect, the invention relates to a method of sensing an analyte in a fluid to be analysed. The method comprises:
- providing a QCM chip implemented as an affinity biosensor as described,
- contacting the interface with the fluid to be analyzed, thereby allowing adsorption of the analyte on the interface, the adsorption being confined to the nanoscale regions; and
- determining an amount (e.g. mass, moles) of adsorbed analyte.

Preferably, the interface is rinsed after the interface has been contacted with the fluid to be analysed and the amount of adsorbed analyte is determined after the rinsing. It should be noted that a determination of the amount of adsorbed analyte can also be carried out before and/or during the rinsing. Preferably, the amount of adsorbed analyte is determined continuously or repeatedly during the adsorption process and the rinsing so as to monitor the (apparent) amount of adsorbate over time.

Preferably, to take full benefit from the confinement effect, the ratio of the average diameter of the nanoscale regions to the size of the analyte is situated in the range from 3 to 50, preferably in the range from 3 to 30, more preferably in the range from 3 to 20, even more preferably in the range from 5 to 15 and still more preferably in the range from 5 to 12. In this context, the size of an analyte is considered to correspond to its largest dimension (diameter). If the analyte is part of a larger compound, e.g. attached to a larger particle or molecule, it is the largest dimension of the compound that counts for the computation of the above ratio.

The sensing could be carried out in static conditions (essentially no flow of the fluid) or dynamic conditions (flowing fluid). Sensitivity may be increased in static conditions.

BRIEF DESCRIPTION OF THE DRAWINGS

By way of example, preferred, non-limiting embodiments of the invention will now be described in detail with reference to the accompanying drawings, in which:

FIG. 4 (c) shows that the nanoparticle densities observed by QCM correspond to those obtained by SEM.

DETAILED DESCRIPTION OF PREFERRED EMBODIMENTS AND EXAMPLES

Figure 14:
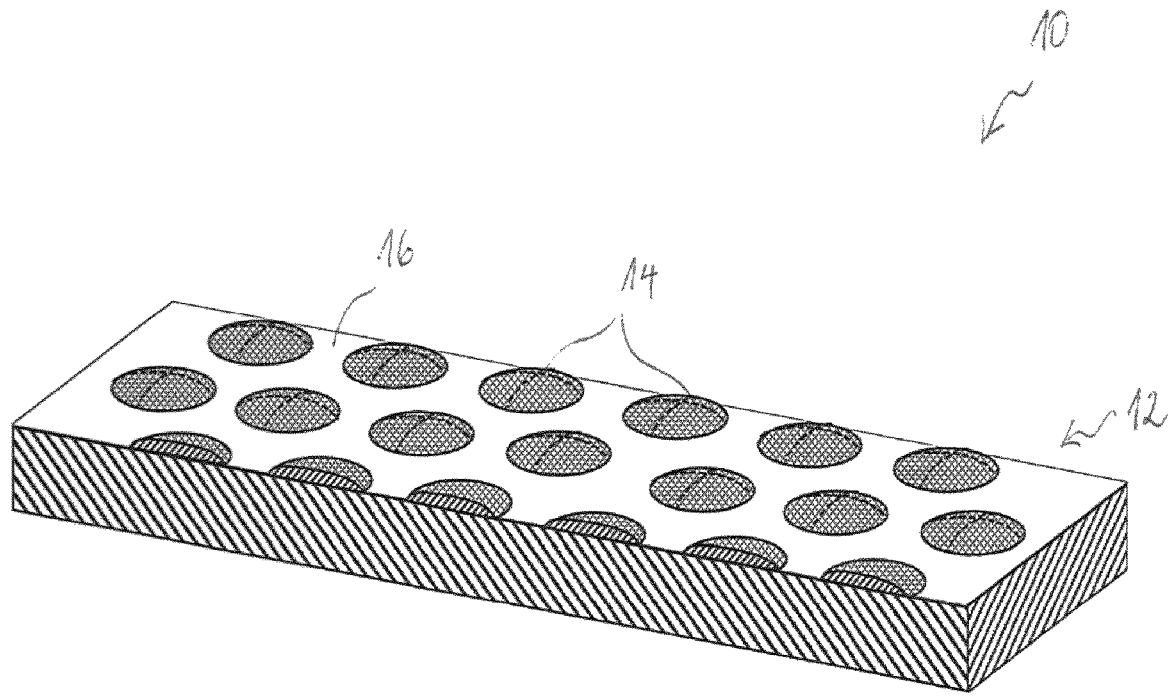
FIG. 14: is a schematic perspective, partially cross-sectional view of a nanopatterned QCM sensor interface.

FIG. 14 shows a detail of a QCM sensor for sensing an analyte in a fluid. The QCM sensor has an interface 12 for contacting the fluid and adsorption of the analyte. The interface is composed of nanoscale regions 14, which the analyte may be adsorbed to, and a passivated region 16. The nanoscale regions 14 are isolated from one another by the passivated region 16 like islands in a sea. Thanks to the passivation, adsorption of the analyte on the interface is confined to the nanoscale regions 14. The nanoscale regions have diameters from 5 to 200 nm. Preferably, the diameters amount to only a few times (e.g. up to 20 times) the size of the analyte. The size and the density of the nanoscale regions are chosen such that the nanoscale regions together have a surface area amounting to at least 10% of the surface area of the entire interface 12.

Example 1

Adsorption of Gold Nanoparticles on QCM Sensor Surface

Binary nanopatterns enabling selective adsorption onto nanoscale regions may be prepared using self-assembled copolymer colloidal templates on a QCM chip surface. Details on this approach that allows creating high-density patterns of nanoscale features spanning large areas can be found, for instance in the papers by Yap, F. L.; Thoniyot, P.; Krishnan, S.; Krishnamoorthy, S. Nanoparticle, "Cluster Arrays for High-Performance SERS through Directed Self-Assembly on Flat Substrates and on Optical Fibers," ACS Nano 2012, 6 (3), and by Nurmawati, M. H.; Ajikumar, P. K.; Renu, R.; Valiyaveettil, S., "Hierarchical Self-Organization of Nanomaterials into Two-Dimensional Arrays Using Functional Polymer Scaffold," Adv. Funct. Mater. 2008, 18 (20), 3213-3218.

The organic copolymer templates on the surface may be converted to patterns that enable confined, selective adsorption on well-defined nanoscale features on surface. By selecting templates with low standard deviation in size (height, diameter and pitch), the dimensions of the features (nanoscale regions) and the feature density (number of features per unit area) will be relatively uniform. In practical experiments, standard deviations down to 5-15% for the different geometric variables (height, diameter and pitch) could be demonstrated. This allows the surface area of the nanoscale regions to be readily calculated, and to correlate this with the QCM measurements.

Specifically, an array of polystyrene-block-polyvinylpyridine (PS-b-PVP) reverse micelles on surface were immersed in water at neutral pH to generate an array of positive charges, due to the basic pyridyl groups present within the core of reverse micelles. Details on this process can be found in the paper by Meiners, J. C.; Quintel-Ritzi, A.; Mlynek, J.; Elbs, H.; Krausch, G., "Adsorption of Block-Copolymer Micelles from a Selective Solvent," *Macromolecules* 1997, 30 (17), 4945-4951. The positive charged features can attract negatively charged citrate-stabilized gold nanoparticles selectively onto the features due to electrostatic attraction.

This approach was used to study the impact of confining the adsorption of gold nanoparticles (with diameters of 10.9±1.7 nm) on the resulting feature densities and the kinetics, as compared to an un-patterned positively charged control surface. The adsorption density and kinetics were measured using a QCM-D. The gold coated QCM chips were coated with reverse micelle films of PS-b-P2VP (Poly (styrene-block-2-vinyl pyridine), 248 KDa-b-195 KDa, obtained from Polymer Source Inc. (Montreal, Canada), 0.5 mg/ml in m-xylene). The periodicity of the arrays can be controlled by evaporation speeds, which, in turn, can be varied by spin-coating speeds. The coated surface was then exposed to reactive ion etching (RIE) for 20-30 s in an oxygen plasma atmosphere, using 20 W and a gas pressure at 15 sccm in a Plasmatherm 790 (St. Petersburg, Fla., USA). The adsorption of gold nanoparticles on the thus prepared interface was then measured.

Figure 1:
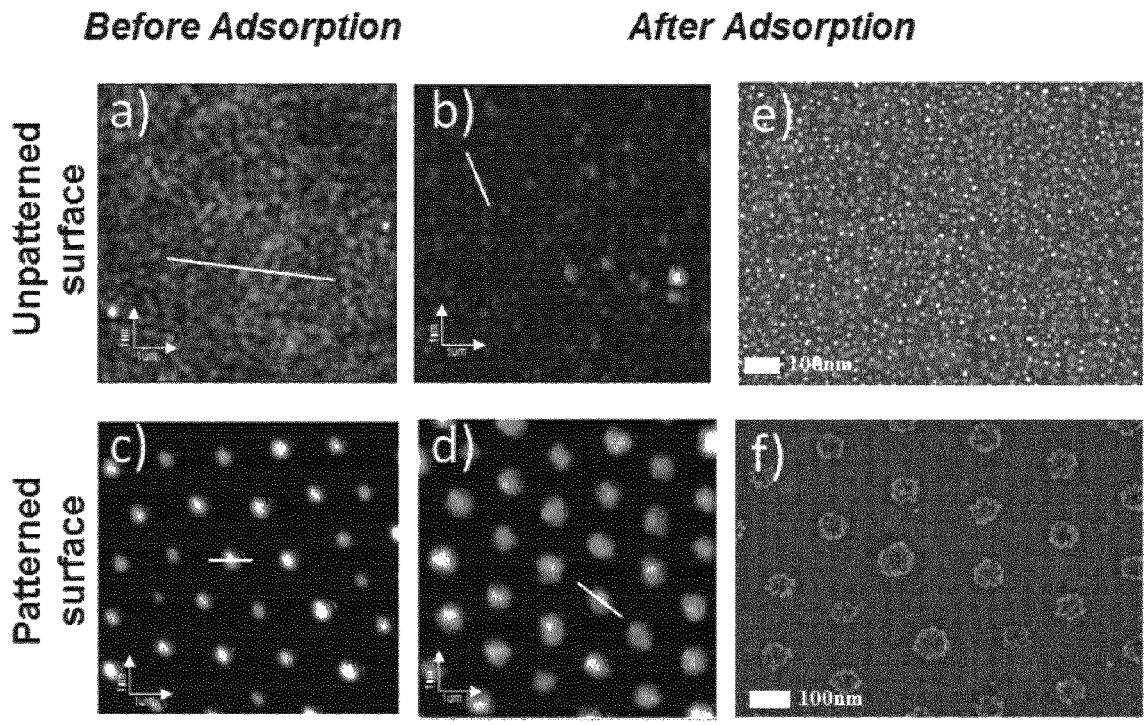
FIG. 1: shows AFM images of unpatterned and patterned QCM chip surfaces before (a) and c)) and after (b), d)) deposition of Au nanoparticles as well as SEM micrographs (e) and f)) of the same surfaces as in b) and d), respectively.

FIG. 1 show AFM images of unpatterned (a), b)) and patterned (c), d)) QCM chip surfaces before (a) and c)) and after (b), d)) deposition of Au nanoparticles. FIGS. 1 e) and f) show SEM micrographs of the same surfaces as in b) and d), respectively. The end point of the adsorption of nanoparticles onto the nanopatterned surface were measured using SEM and AFM and it was confirmed that the adsorption indeed occurred selectively onto the reverse micelle features.

Figure 2:
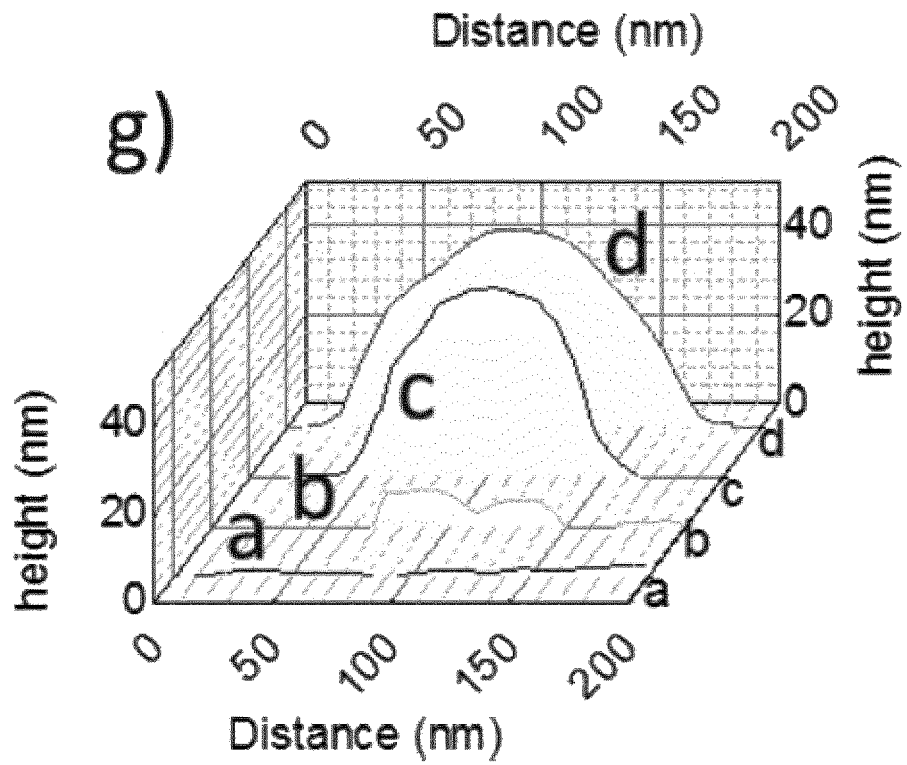
FIG. 2: is a representation of the height profiles along the lines indicated in FIGS. 1 a), b) c) and d), respectively.
Figure 3:
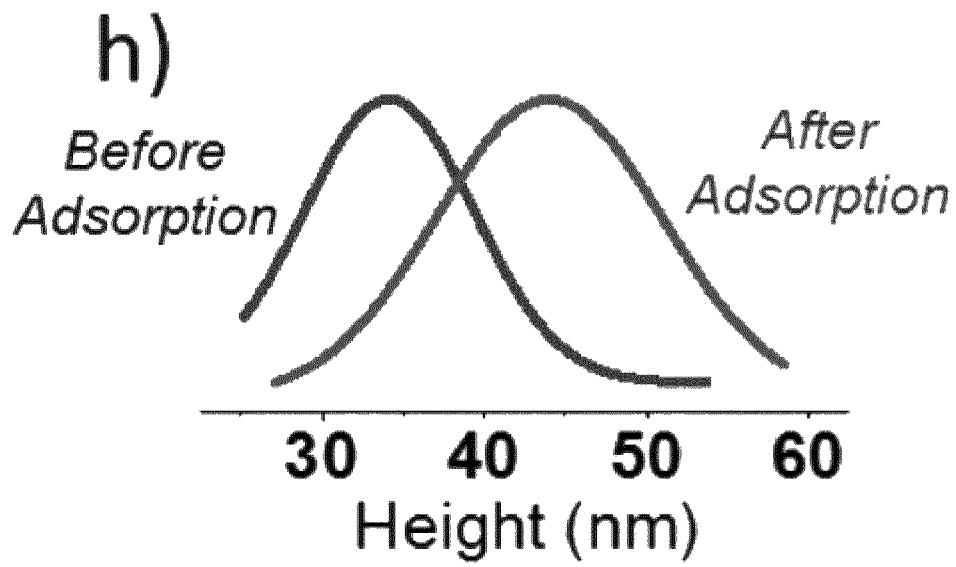
FIG. 3: is an illustration of the distribution of the heights of the nanodots before and after adsorption of the gold nanoparticles.

FIG. 2 shows the height profiles along the lines indicated in FIGS. 1 a), b) c) and d), respectively. FIG. 3 illustrates the distribution of the heights of the dots before and after adsorption of the gold nanoparticles. It can be seen that the mean height of the dots is increased by about the average diameter of the nanoparticles.

Figure 4:
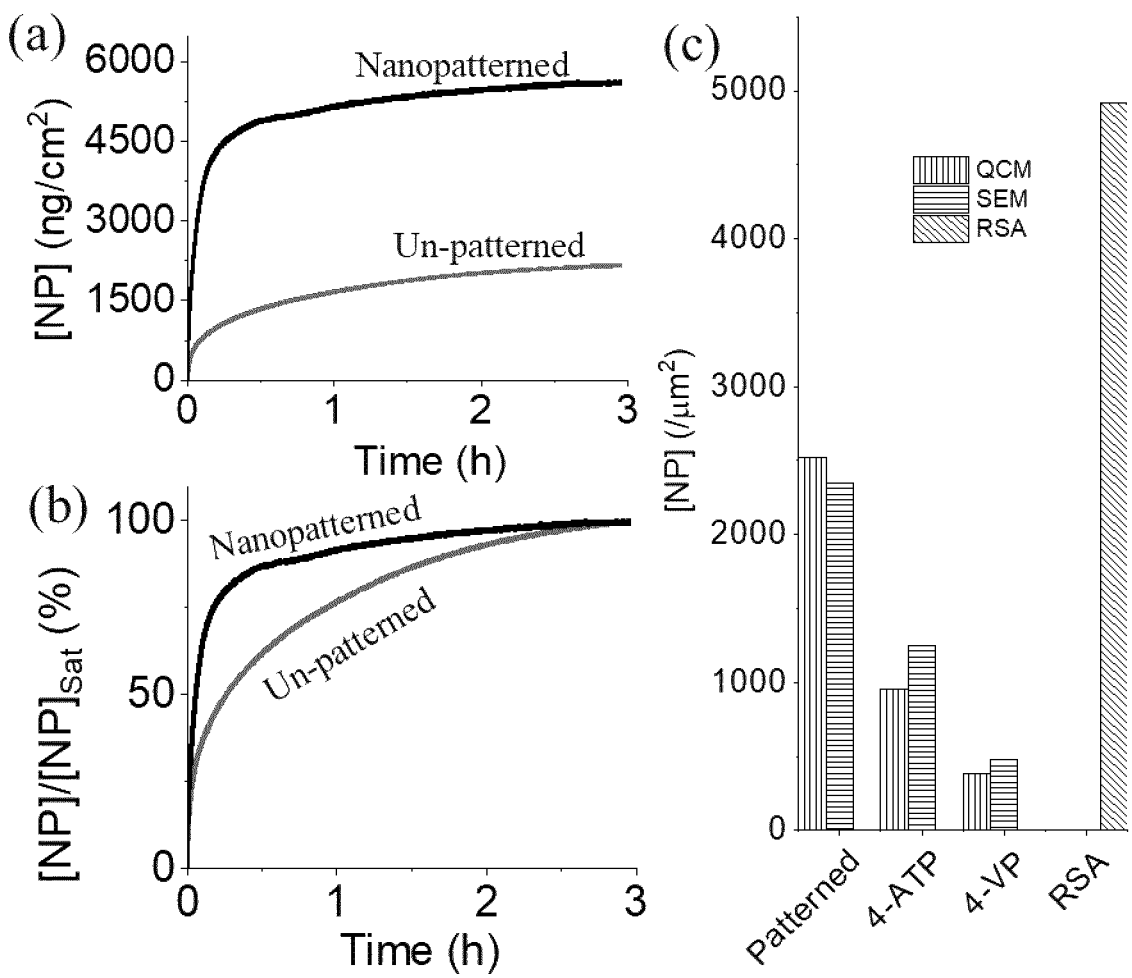
FIG. 4: shows a comparison of the density (a) and kinetics (b) of adsorption of gold nanoparticles from suspensions of 0.85 mM concentration on patterned and un-patterned sensor surfaces, as measured by QCM.

FIG. 4 illustrates a comparison of the density (a) and kinetics (b) of adsorption of gold nanoparticles from suspensions of 0.85 mM concentration (0.85 millimole of gold nanoparticles per litre) on patterned and un-patterned sensor surfaces, as measured by QCM. The decrease in QCM sensor frequency was converted to mass using Sauerbrey's equation. The curves of FIG. 4 (a) were normalized to the respective active surface area. The curves of FIG. 4 (b) were obtained by dividing the adsorbed mass by the (estimated) mass per nanoparticle to arrive at the number of nanoparticles (NP) and by normalizing to the respective saturated configuration.

FIG. 4 (c) shows that the nanoparticle densities observed by QCM were in reasonable agreement with those obtained by SEM. The results were further compared with those obtained on the un-patterned control surfaces (gold surface covered with a uniform self-assembled 4-aminothiophenol (4-ATP) monolayer or with a uniform self-assembled 4-vinylpyridine (4-VP) monolayer).

The adsorption curve obtained for the patterned surface was normalized to the active surface area available for adsorption (i.e. the surface area of the nanodomes). The normalization factor was obtained from the surface area of each nanodome and the density of the nanodomes (number of nanodomes per unit area) as obtained from AFM and SEM measurements. The surface area per nanodome was obtained by modelling the nanodome as a hemisphere, with the height measured from AFM and diameter from SEM.

The nanopattern presented a surface area of 9800 nm$^2$ per nanodome, with 33 nanodomes/μm$^2$. The nanodomes' surface area thus constituted ~33% of the total surface area.

Table 1 summarizes the results obtained for the adsorption Au nanoparticles on patterned interface and un-patterned (uniform) control surface. Values derived from QCM (adsorption curves) are marked "(QCM)" and were cross-checked by SEM. The corresponding values based on SEM are marked "(SEM)" in Table 1.

TABLE 1

| Surface | Nano-patterned | Uniform |
| --- | --- | --- |
| Surface area per nanodome | 9780 nm$^2$ ± 10% | / |
| Surface area available for adsorption | 33% | 100% |
| Density of nanodomes | 33.75/μm$^2$ | / |
| Number of nanoparticles adsorbed (per nanodome) | 23 (SEM) 25 (QCM) | / |
| Theoretical maximum (RSA) number of nanoparticles | 48 (per nanodome) | 4921 (per μm$^2$) |
| Number of nanoparticles per unit surface area available for adsorption (at saturation) | 2518/μm$^2$ (QCM) 2350/μm$^2$ (SEM) | 958/μm$^2$ (QCM) 1250/μm$^2$ (SEM) |
| Nanoparticle coverage with respect to theoretical maximum (RSA) | 51% (QCM) 48% (SEM) | 19% (QCM) 25% (SEM) |

TABLE 1-continued

| Surface | Nano-patterned | Uniform |
| --- | --- | --- |
| Nanoparticle coverage per unit surface area available for adsorption | 28% (QCM) 26% (SEM) | 11% (QCM) 14% (SEM) |

Due to the nanopatterning, the density of nanoparticles at saturation could be increased by 188% (based on the SEM micrograph counts: 188%=2350/1250). Further, a coverage of 95% (with respect to the saturation value) was attained in 85 minutes on the patterned surface, while it took 130 minutes on the un-patterned counterpart, thus confirming a clear increase in the kinetics of adsorption.

Figure 5:
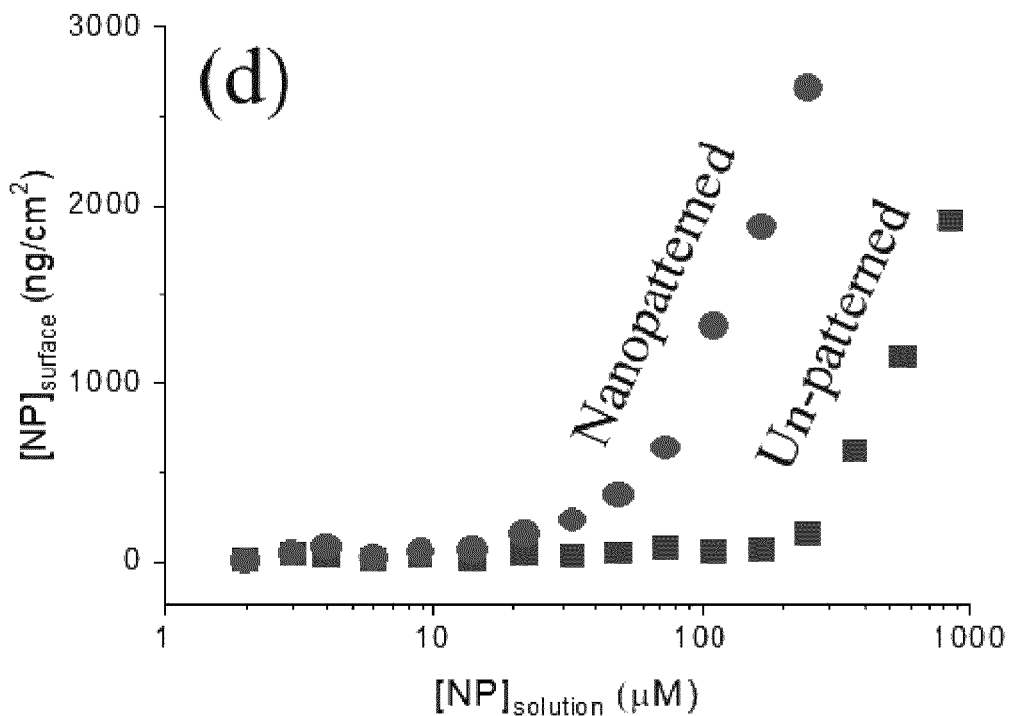
FIG. 5: is a graph representing the adsorption densities as a function of suspension concentration.
Figure 6:
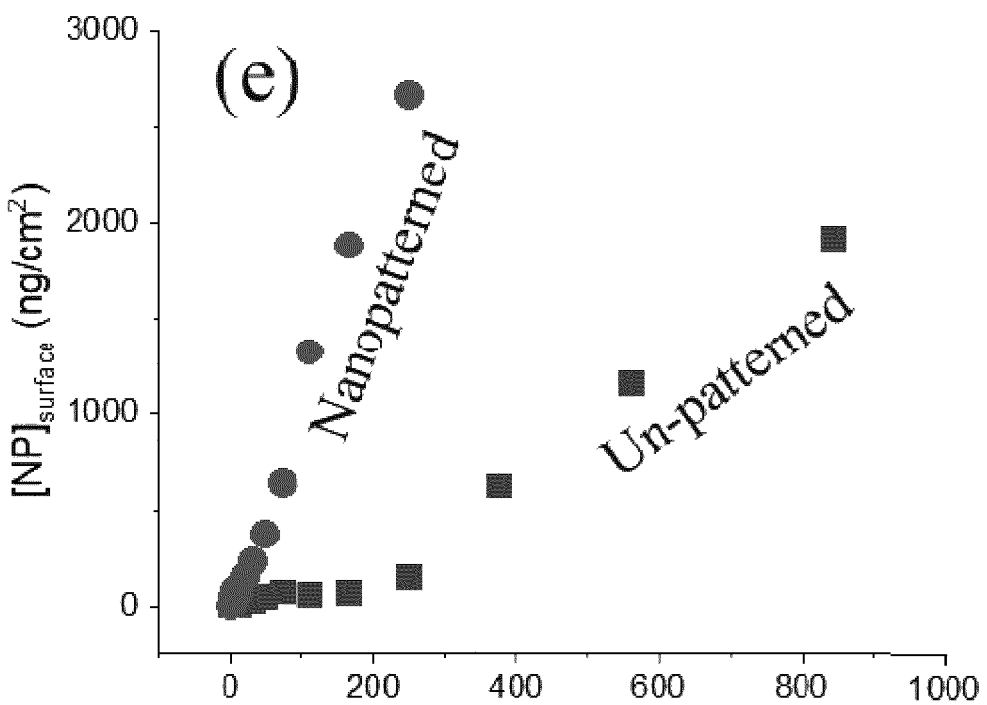
FIG. 6: is a the graph of FIG. 5 with a linear scale on the x-axis.

Furthermore, the nanopatterned sensor interfaces were observed to be sensitive at concentrations an order of magnitude lower than the un-patterned ones (see FIGS. 5 and 6). The change in surface density versus analyte concentration, in the linear regime, had a slope of 11.2 ng/($\mu M \cdot cm^2$) for the nanopatterned interface, whereas the slope was only 2.8 ng/($\mu M \cdot cm^2$)) for the un-patterned surface. This represents a 6-fold increase in sensitivity due to the nanopatterns. The nanopatterns, despite their lower surface coverage (of ~33% in the example) reach nanoparticle densities on par or higher than that of the uniform surface.

If one assumes that nanoparticle adsorption to the sensor interface can be modelled by random sequential adsorption (RSA) processes, the maximum surface coverage (theoretical limit, "jamming limit") is 54.7%. The nanoparticle coverage at saturation approached 28% (corresponding to 51% of the jamming limit) on the nanodomes, whereas in the case of the un-patterned interface, the nanoparticle coverage amounted to only 11% (corresponding to 19% of the jamming limit).

Example 1a

Adsorption of Gold Nanoparticles on QCM Sensor Surface Under Flow

Figure 10:
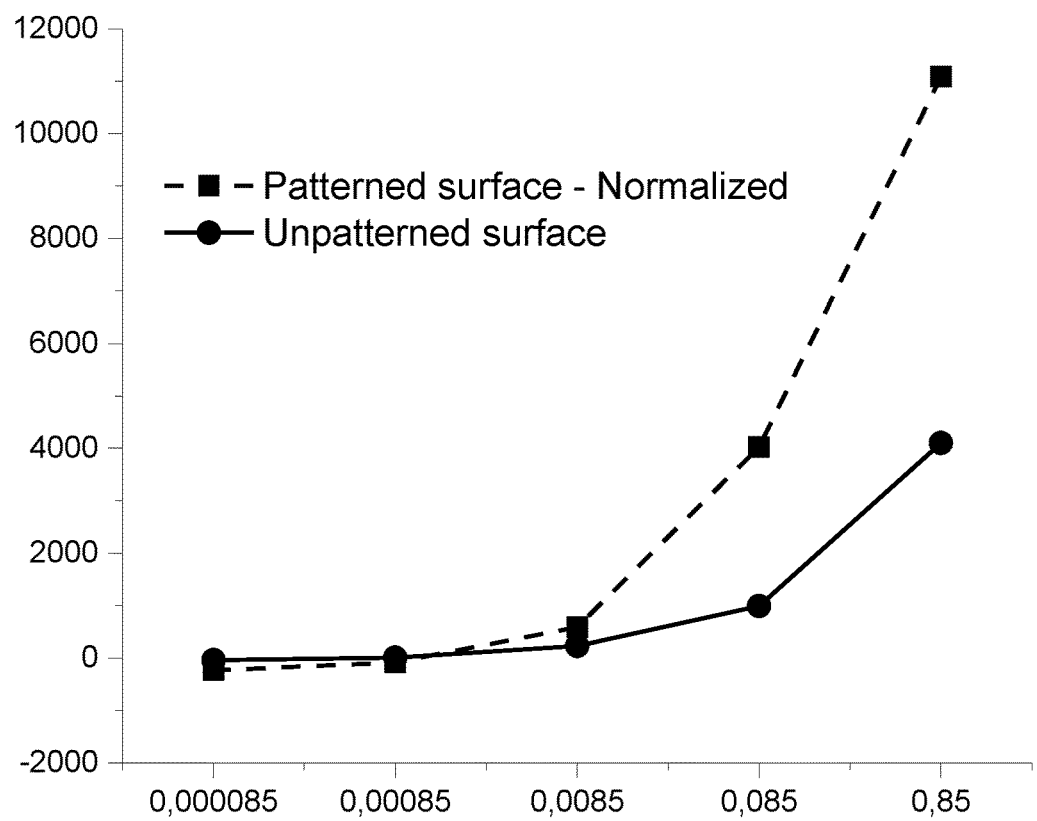
FIG. 10: shows the mass density of Au nanoparticles deposited under flow, normalized by the surface area available for adsorption, at saturation as a function of concentration.
Figure 11:
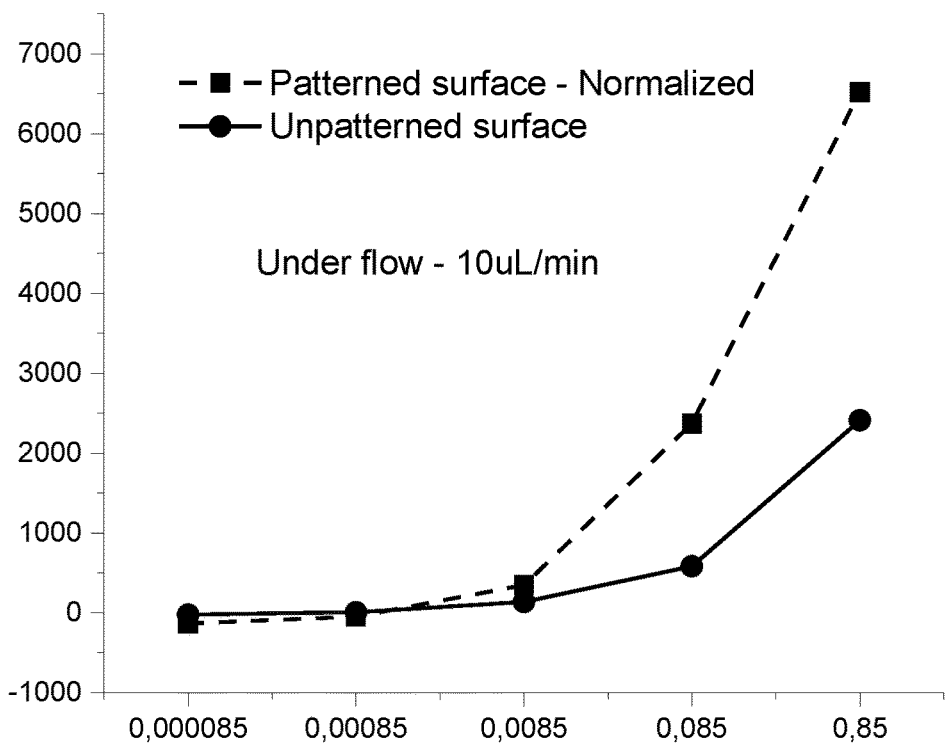
FIG. 11: shows the density of adsorbed Au nanoparticles of FIG. 10, normalized by the surface available for adsorption and the corresponding surface coverage (as a percentage of the jamming limit).

The experiments of example 1 were made in static conditions. The experiments were repeated under flow conditions. Binary patterns were prepared on QCM chips as described in example 1. The nanoscale regions with affinity for the gold nanoparticles had a surface area amounting to 33% of the total interface surface area. Gold nanoparticles were deposited from suspensions with concentrations between 85 nM and 0.85 mM. The flow of the suspensions was set to 10 µL/min (microlitres per minute), the chamber above the sensor surface had a volume of 40 µl and the temperature was held constant at room temperature. The deposition of the gold nanoparticles was monitored by QCM-D. FIG. 10 shows the deposited mass density, normalized by the surface area available for adsorption, at saturation as a function of concentration. It can be seen that significantly higher adsorption densities than on an un-patterned surface may also be obtained under flow. This result indicates microfluidic devices may benefit from the invention. FIG. 11 is based on FIG. 10 and shows the density of adsorbed nanoparticles, normalized by the surface available for adsorption and the corresponding surface coverage (as a percentage of the jamming limit).

Example 1

Impact of the Fill Factor of the Nanopattern

QCM-D measurements of the adsorption of gold nanoparticles were made as in the previous examples using nanopatterned sensor interfaces with different fill factors. The first binary pattern corresponds to the one used in examples 1 and 1a and had a fill factor of 33%. A second nanopattern had a fill factor of 61%: the nanoscale regions having affinity for the gold nanoparticles were of the same size as those of the first binary pattern but the density of the regions was increased. It was observed that the overall adsorption (taking the entire sensor interface into account) increases when the fill factor is increased. To understand if there is an influence of the fill factor on the adsorption density within the regions having affinity, the adsorbed masses were normalized by the surface area available for adsorption. No significant difference was noted, which indicates that the density of adsorbed nanoparticles within each feature remained the same for the tested fill factors. The positive impact of the nanopattern on the adsorption density remains when the fill factor is increased to 61%. This is a noteworthy result, since it allows reducing the "inactive" regions (where no adsorption occurs), without compromising the effect of preferential adsorption onto nanopatterns.

Figure 12:
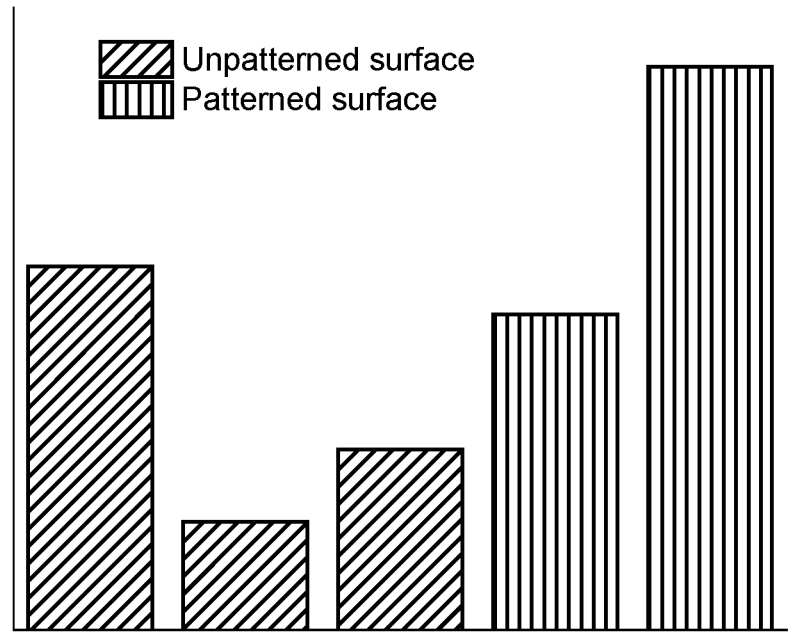
FIG. 12: shows the adsorbed mass of Au nanoparticles at saturation for different unpatterned interfaces and two nanopatterned interfaces having different fill factors (without normalization by the available surface area).
Figure 13:
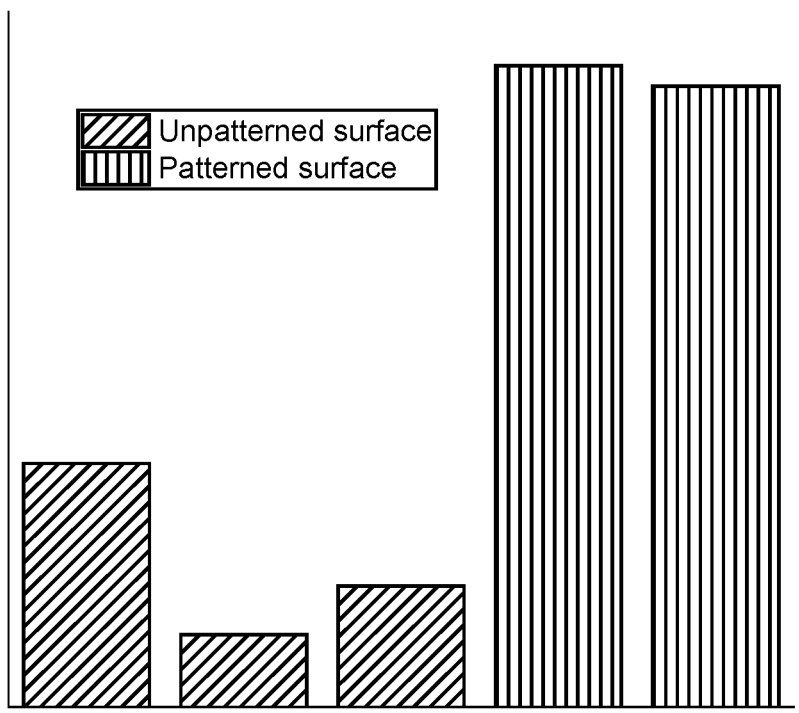
FIG. 13: shows the adsorbed masses of FIG. 12, after normalization by the available surface area.

FIG. 12 shows the adsorbed mass at saturation for different unpatterned interfaces and the two nanopatterned interfaces, without normalization by the available surface area. The nanopattern with the fill factor of 33% is labelled "D0.5" while the one with the fill factor of 61% is labelled "D1.4". It may be worthwhile noting that the footprint (vertical projection of areas having affinity with respect to substrate) of the D0.5 nanopattern amounts to 16% It can be seen that the overall adsorbed mass on the nanopatterned interface having the fill factor of 61% even exceeds the mass adsorbed on the uniform interfaces. FIG. 13 shows the adsorbed masses at saturation after normalization by the available surface area.

Example 2

Protein Adsorption (BSA)

While example 1 demonstrates the effect of nanoscale confinement on electrostatic attachment of nanoparticles, it needed to be proven that such an effect can be obtained with different types of adsorption events. In this example, the impact of nanoscale confinement on physisorption of two different biomolecules, bovine serum albumin (BSA) and immunoglobulin (IgG) was investigated.

In a first step, nanopatterns that can confine biomolecular adsorption to pre-defined regions of the sensor interface were fabricated.

A binary pattern was obtained by the usage of silica and gold, whereas the un-patterned control for this series of experiences was a bare silica surface.

Figure 7:
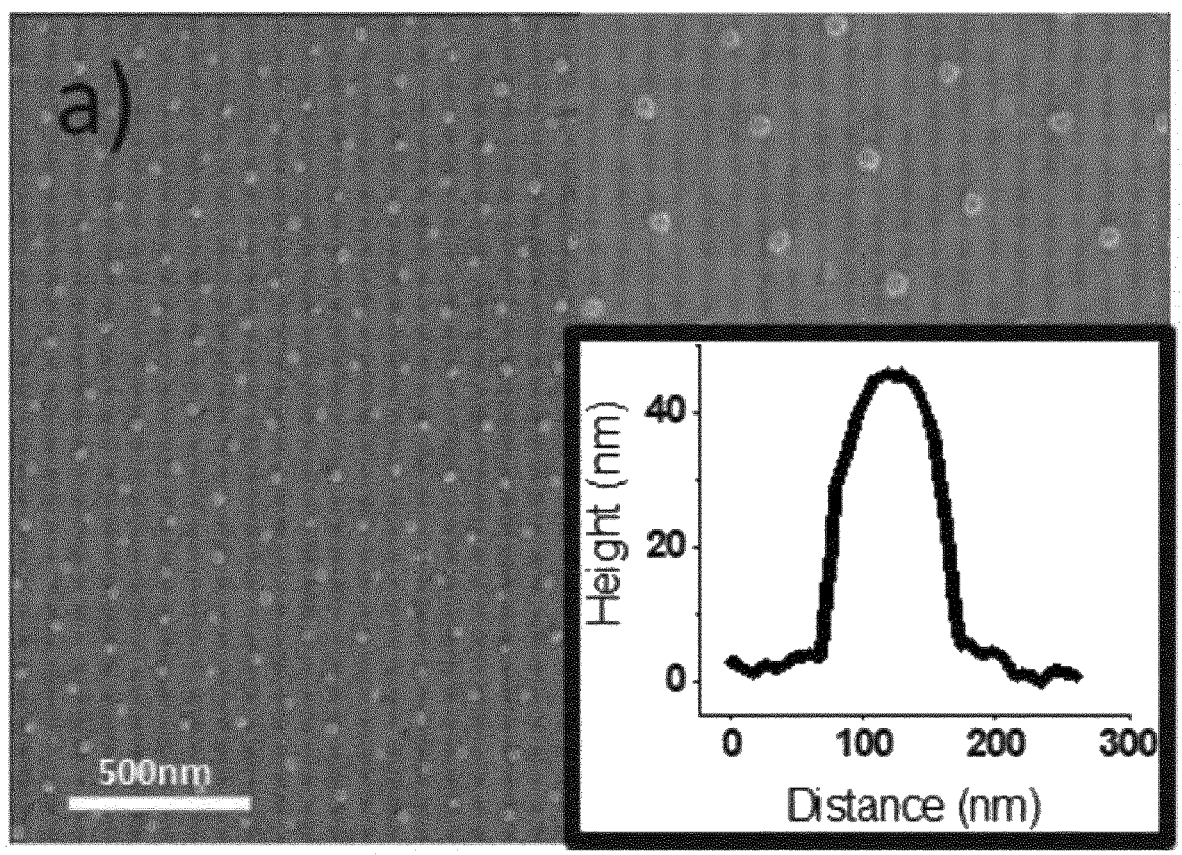
FIG. 7: shows a pattern of silica nanodomes on a gold-coated substrate (left-hand side) obtained by SEM, a height profile of a nanodome obtained by an AFM linescan (bottom right) and a higher-resolution detail of the pattern (top right).

By taking advantage of PS-b-PVP self-assembly, resulting in a hexagonal-lattice packing of reverted micelles, on the gold surface of a QCM chip, a hard material contrast pattern was generated: silica nanoregions on gold surface. The PS-b-PVP coated gold surface was exposed to a tetraethyl orthosilicate (TEOS) atmosphere for 6 hours to allow diffusion of silicate into the reverted micelles and to thereby obtain a hexagonal lettuce of silica nanoregions which is an image of the reverted micelles pattern. The mechanism is explained in more detail in Cha, J. N.; Zhang, Y.; Philip Wong, H. S.; Raoux, S.; Rettner, C.; Krupp, L.; Deline, V., "Biomimetic Approaches for Fabricating High-Density Nanopatterned Arrays," Chem. Mater. 2007, 19 (4), 839-843. The hydrolysis of TEOS occurs in the nucleophilic cores of the micelles (i.e. in the vinylpyridine domains), essentially without modifying the outer polystyrene shells and thus allowing the latter to be removed by oxygen plasma. The topography and top-view of the silica nanodomes produced (SiNDs from now on) is shown in FIG. 7.

The height of the SiND was found to amount to 35±5 nm and the diameter to 40 nm±4.3 nm.

To prevent the physisorption of BSA and IgG, the gold area between the SiND is selectively functionalized with protein-resistant polyethylene glycol (PEG) moieties bound to the gold surface by thiol groups. The efficiency of the protein-resistant PEG coating was tested and was found to amount to 80%. The efficiency is measured as:

$$\frac{m_{BSA\ on\ PEG}}{m_{BSA\ on\ Au}},$$

where $m_{BSA}$ on PEG is the adsorbed BSA mass on a surface functionalized with protein resistant molecules (PEG). $m_{BSA\ on\ Au}$ is the adsorbed BSA mass on a regular gold surface (standard). The efficiency of the passivation is preferably at least 80% as measured above. By passivating the gold region, the adsorption of biomolecules is forced to occur (almost exclusively) on the SiND, which, in this example, represent ~17% of the interface (taking the 3D shape thereof into account).

Figure 8:
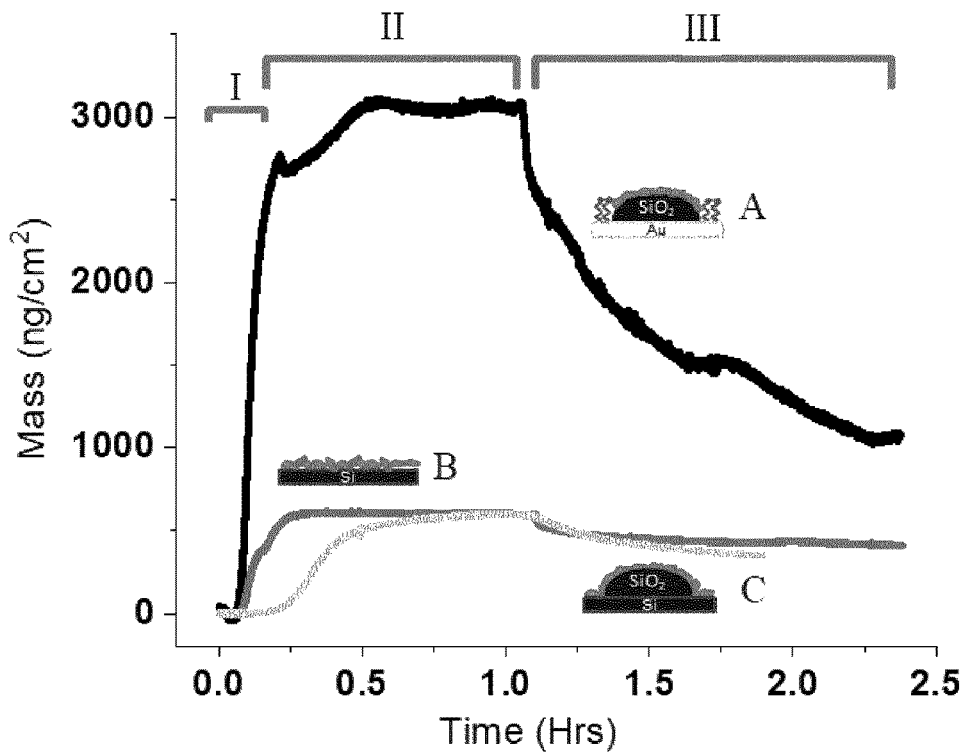
FIG. 8: shows BSA adsorption curves measured by QCM-D for (A) a nanopatterned sensor surface wherein the gold area between the SiND is passivated with PEG, (B) an unpatterned control surface (made of Si), and (C) a nanopatterned comparison surface with SiND on Si, without passivation of the silicon area between the SiND.

FIG. 8 shows BSA adsorption curves measured by QCM-D for:
A. the nanopatterned sensor surface wherein the gold area between the SiND is passivated with PEG;
B. an unpatterned control surface (made of Si); and
C. a nanopatterned comparison surface with SiND on Si, without passivation of the silicon area between the SiND.

The adsorbed masses in FIG. 8 are normalized to take into account the surface area respectively available for adsorption.

The adsorption tests with BSA were carried out as follows: BSA was dissolved in PBS (phosphate-buffered saline) 1 mg/ml, and flowed at a rate of 10 μL/min flow rate for 1 h (phases I and II in FIG. 8). In a second step, PBS was flowed for 60 min to remove BSA in excess. BSA adsorption on the unpatterned control (FIG. 8, curve B) gives an adsorption density of 400 ng/cm², whereas the adsorption density on the nanopatterned sensor surface amounts to 180 ng/cm² in confinement conditions (FIG. 8, curve A). Considering that the SiND represent ~17% of the sensor interface, one would have expected, based on the values of the unpatterned control surface and taking into account imperfections in the passivation layer, an adsorption density of 65 ng/cm² rather than the 180 ng/cm² that were measured. The binary nanopattern thus caused an increment of 190% in terms of adsorption density. Curve C in FIG. 8 shows the adsorption of BSA on SiND on silicon substrate without passivation. If one considers the surface area increase with respect to the flat substrate due to the SiND, one finds an adsorption behaviour that is very similar to that of the unpatterned control surface. This demonstrates the importance of having a binary pattern with nanoscale regions having affinity for the analyte and a passivated region that surrounds them. The apparent decrease in adsorbed mass during the rinsing phase (FIG. 8, phase III) can be explained by the presence of BSA loosely bound or at a short distance to the sensor surface during phases I and II. This "apparent" mass disappears when the flow is switched to buffer solution (phase III).

The expected mass comes up when a pattern is considered and is calculated as:

$$m_{exp} = m_{unpatt} S_{feature}$$

Where $m_{unpatt}$ is the mass which adsorbs on the unpatterned control and $S_{feature}$ is the surface available for adsorption on the patterned control. The percentage of enhancement in terms of density is then calculated as:

$$\%_{enh} = \frac{(m_{patt} - m_{unspec} \cdot S_{bck})}{m_{exp}} \cdot 100$$

The percentage of enhancement is expressed as above where: $m_{patt}$ is the mass which is obtained experimentally, $m_{unspec}$ is the mass accumulated not selectively on passivated areas, $S_{bck}$ is the passivated surface area and $m_{exp}$ is the expected mass as defined above.

Example 3

Physisorption of Bcl-2 Capture Antibody

A nanopatterned QCM sensor interface was prepared as in Example 2 (silica nanodomes on a gold-coated substrate, the exposed gold surface being passivated with an anti-fouling layer). For comparison, a QCM chip with a bare silica surface underwent the same experiment.

Figure 9:
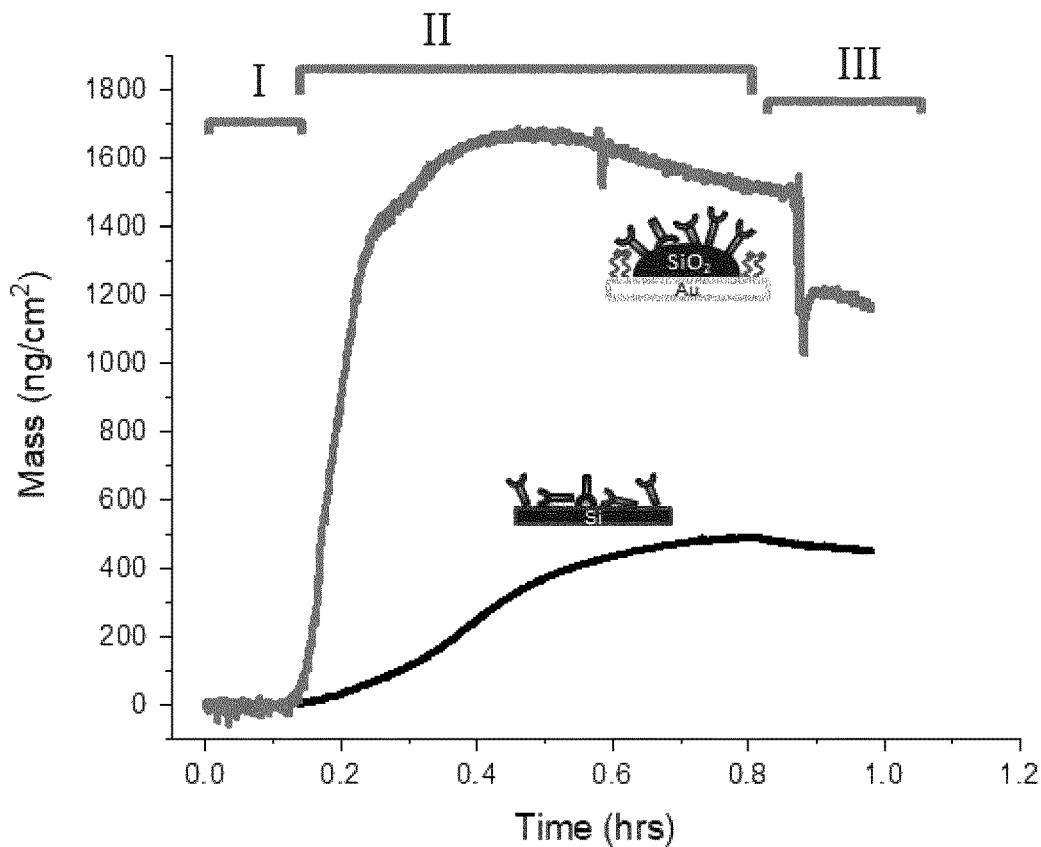
FIG. 9: shows the evolution of adsorbed masses of Bcl-2 antibody (measured by QCM-D) on a nanopatterned interface (top curve) and on a homogeneous Si interface (bottom curve).

Human Total Bcl-2 capture antibody was reconstituted in PBS, and then diluted to 27 μg/ml for use. Bcl-2 capture antibody was brought to the test surfaces by a flow at 10 μL/min for 30 min, then the flow was switched to buffer for 20 min. FIG. 9 shows the evolution of the adsorbed masses (as measured by QCM-D) on the nanopatterned interface (top curve) and on the homogeneous Si interface (bottom curve). The antibody was injected in during phase II. During phase III, the system was rinsed with buffer solution.

In this example, the figures of merit were the same reported above in example 2. $m_{unpatt}$ was equal to 450 ng/cm². $m_{patt}$ was 185 ng/cm². If one considers a similar efficiency in the protein resistant layer (85% efficiency), the expected mass is equal to 125 ng/cm². The percentage of enhancement then sits at 180%. The efficiency of the protein resistant layer is $m_{unspec}$ is calculated as:

$$\%_{efficiency} = \frac{m_{unpatt}}{m_{anti-fouling}},$$

where $m_{unpatt}$ is the adsorbed mass on the unpatterned control and $m_{anti-fouling}$ is the mass adsorbed on a control specifically functionalized with anti-fouling moieties and tested against Bcl-2.

Example 4

Figure 15:
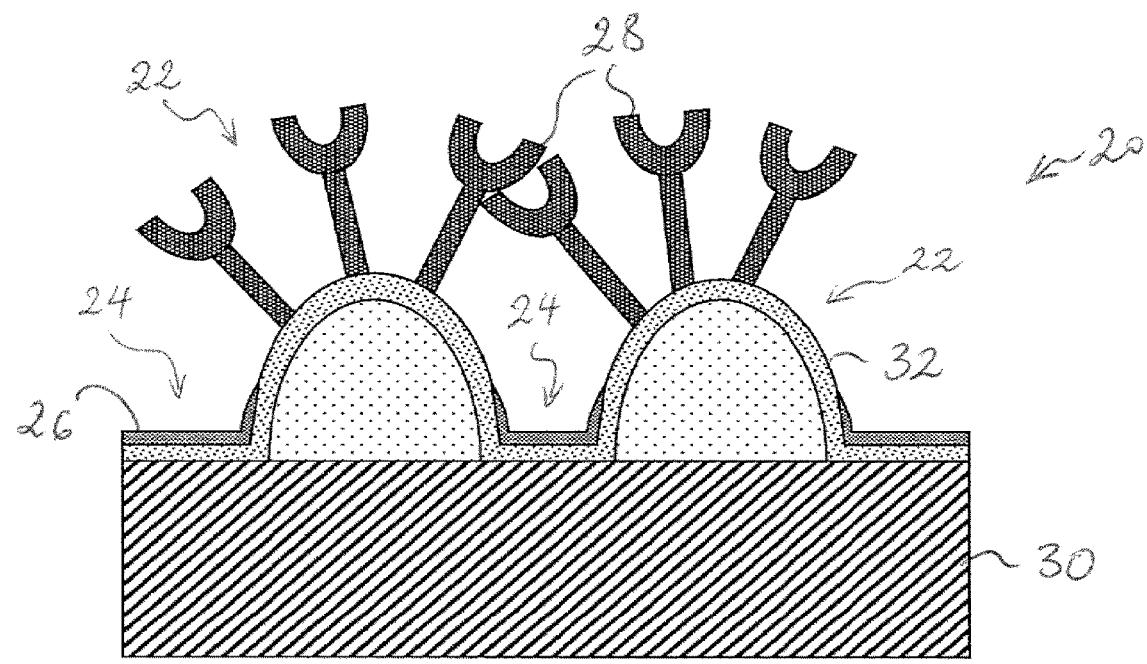
FIG. 15: is a schematic illustration of an affinity biosensor comprising a binary pattern of nanodomes carrying carry capture antibodies specific to a biomolecule.

FIG. 15 schematically shows an affinity biosensor 20 comprising a binary pattern of nanodomes 22. The region 24 between the nanodomes 22 is covered with a passivation layer 26, e.g. a methoxypolyethylene glycol thiol (SH-PEG-CH₃) layer. The nanodomes 22 carry capture antibodies 28 (e.g. goat anti-mouse IgG), having affinity for a biomolecule (e.g. mouse IgG).

The nanodomes were fabricated on the substrate 30 (QCM sensor with gold coating) by PS-b-PVP self-assembly, resulting in a hexagonal-lattice packing of reverted micelles. The surface was then exposed to reactive ion etching (RIE) for 20-30 s in an oxygen plasma atmosphere. The obtained surface was then coated with a thin layer of gold 32 using a vapour deposition process. The gold layer 32 was then coated with the passivation layer.

The removal of the passivation layer on the nanodomes 22 was effected by first coating the entire surface with PMMA, followed by another step of RIE in an oxygen plasma atmosphere. As the thickness of the PMMA layer is highest between the nanodomes, in that region, the passivation layer remains protected by the PMMA until complete etching thereof. As a result, the gold coating is exposed on the nanodomes but remains covered with the passivation layer 26 in-between the nanodomes 22.

In the example, a feature density of 33 features/μm was achieved, with a surface available for adsorption of ~21% of the total interface surface.

Figure 16:
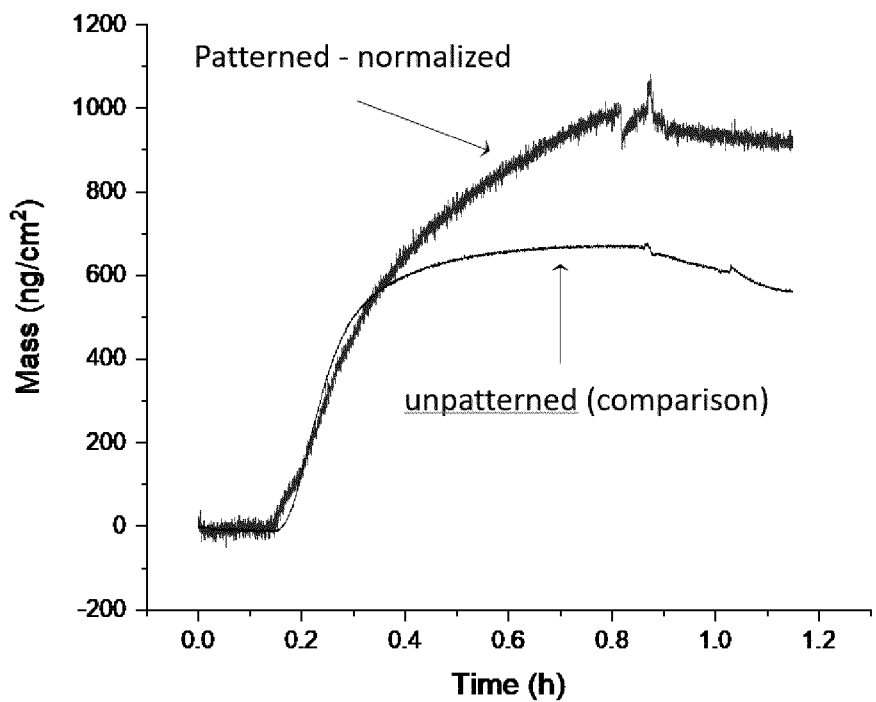
FIG. 16: is a graph showing adsorption of goat anti-mouse IgG antibodies (at 24 μg/mL in PBS) on the surface patterned with nanodomes, in comparison with an unpatterned gold surface.

FIG. 16 shows adsorption of goat anti-mouse IgG antibodies (at 24 μg/mL in PBS) on the surface patterned with the nanodomes, in comparison with an unpatterned gold surface. The resulting biosensor 20 is that schematically shown in FIG. 15.

Figure 17:
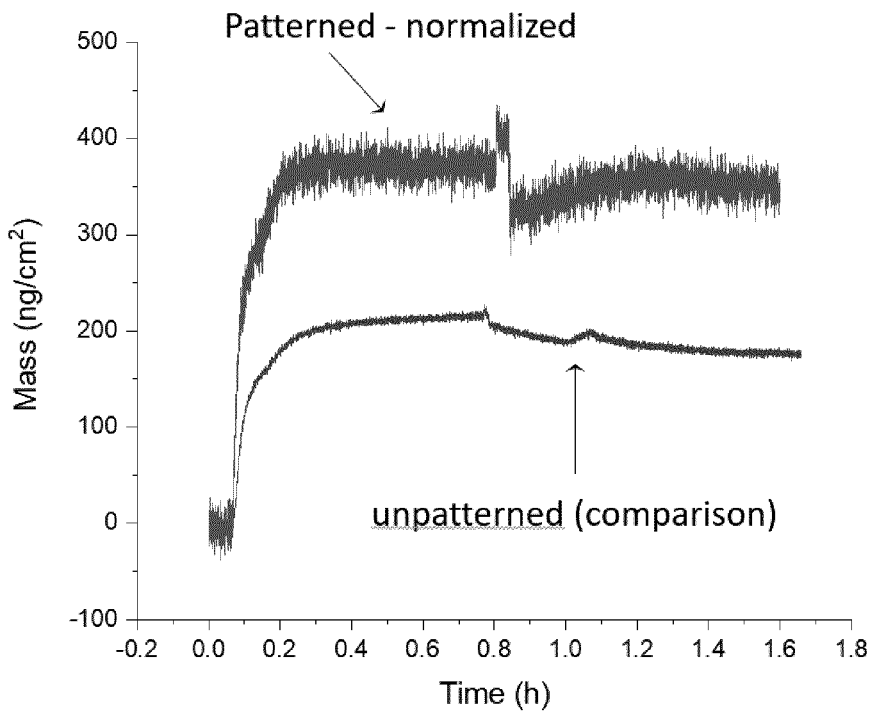
FIG. 17: is a graph showing adsorption of the target biomolecules on the affinity biosensor of FIG. 15, in comparison with an unpatterned reference sample.
Figure 18:
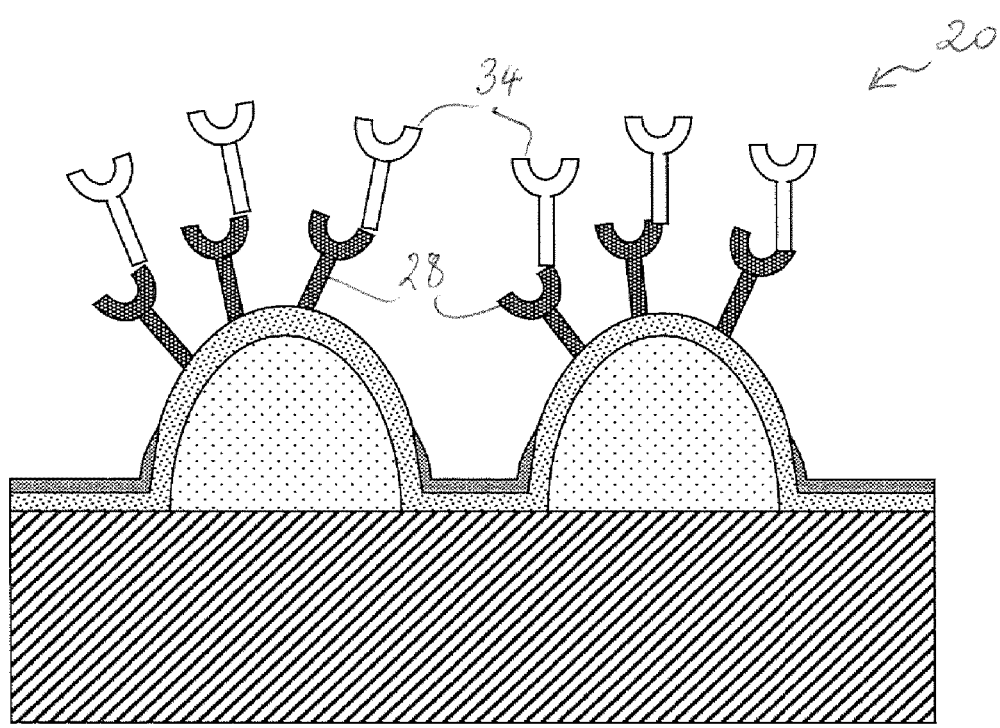
FIG. 18: is an illustration of the target biomolecules bound to the capture antibodies of the affinity biosensor of FIG. 15.

The affinity biosensor of FIG. 15 was tested against mouse IgG (at 25 μg/mL in PBS). The corresponding adsorption plot is shown in FIG. 17 in comparison with an unpatterned reference sample. FIG. 18 illustrates the target molecules 34 bound to the capture antibodies 28.

Materials Used in the Examples

Gold coated quartz crystals (nominal frequency of 5 MHz, AT-cut) were obtained from Quartzpro (Järfälla, Sweden) and employed after a thorough cleaning with acetone and ethanol followed by 30 mins in UV-ozone cleaner obtained from Jelight Company Inc. (Irvine Calif., USA).

Poly(styrene-block-2-vinyl pyridine) (PS-b-P2VP) (248 KDa-b-195 KDa) was obtained from Polymer Source Inc (Montreal, Canada).

4-aminothiophenol (4-ATP), 4-thiolpyridine (4-TP), Tetraethyl orthosilicate (TEOS), and tetrachloroauric(III) acid ($HAuCl_4 \cdot 3H_2O$) were purchased from Sigma-Aldrich.

Spectroscopic grade m-xylene, ethanol and acetone were also obtained from Sigma-Aldrich.

Bovine Serum Albumin (BSA) was purchased from Sigma-Aldrich as well.

Phosphate Buffer Saline (PBS), Human Total Bcl-2 antibodies were purchased from R&D System (Minneapolis, Minn., USA).

Polyethylene glycol thiol (PEG-thiol) in different length and sizes were obtained from BroadPharm (San Diego, Calif., USA): PEG3 with —OH functional group (Mw=166.2) and PEG12 with —COOH functional group (Mw=634.8).

Methods Used in the Examples

Unpatterned control was prepared by immersing gold coated quartz crystal in 4-ATP solution (5 mM in ethanol) for >16 h typically, then washed and blow dried.

Micellar template was obtained by process reported in Meiners, J. C.; Quintel-Ritzi, A.; Mlynek, J.; Elbs, H.; Krausch, G., "Adsorption of Block-Copolymer Micelles from a Selective Solvent," *Macromolecules* 1997, 30 (17), 4945-4951. Briefly, PS-b-P2VP (0.5 mg/ml in m-xylene) were coated on QCM chip. The periodicity of the arrays were controlled by evaporation speeds, which in turn were varied by spin-coating speeds. The surface was then exposed to reactive ion etching (RIE) for 20-30 s in an oxygen plasma atmosphere, using 20 W and a gas pressure at 15 sccm, using Plasmatherm 790 (St. Petersburg, Fla., USA).

Gold nanoparticles of 10 nm diameter were produced using sodium citrate as reducing agent.

Silica particles on gold substrate: PS-b-P2VP pattern is created on specific surface and then left for different amount of time (1-24 h) in a dessicator in presence of TEOS and water (1 mL each) in a oven at 60° C. Once the samples are removed from the dessicator, they are exposed to $O_2$ plasma for 3 minutes to ensure a complete removal of the polymer constituting the shell, to obtain an $SiO_2$ particle array with a periodicity matching that of the original template.

Surface preparation for protein physisorption: Silica particles on gold substrate were obtained as described above. The surface was then dipped in polyethylene glycol thiol solution (5 mM in water) for 4 h until the surface of the sample not occupied by silica particles was taken by PEG molecules and made protein resistant.

Protein physisorption: Before introducing biomolecules in the flow, the system was let to stabilize for variable time until a good baseline was achieved. Bovine Serum Albumin (BSA) was dissolved in PBS (1%) and let physisorbing on the surface for 1 h, then the surface was rinsed with buffer until a stable signal was achieved (up to 60 min of buffer flowing). Typical flow rate was 10 μL/min. Human Total Bcl-2 capture antibody was reconstituted in PBS and then diluted to 27 μg/mL for usage. Bcl-2 capture antibody was ran for 30 min at 10 μL/min, then the flow was switched to a buffer solution for 20 min.

Characterization of the patterns: The nanopatterns was investigated by atomic force microscopy using Innova, Bruker system (Paris, France) and aluminium coated silicon probes (10-130 N/m) from Nanosensors (Neuchatel, Switzerland) in tapping mode. Scanning electron microscopy micrographs were obtained by using a Helios 650 FIB-SEM (from Hillsboro, Oreg., USA) typically at 2-5 kV accelerating voltage and 25 pA beam current. The QCM measurements were made with a Quartz Crystal Microbalance with dissipation module (QSense Explorer, QCM-D), obtained from Biolin Scientific AB (Gothenburg, Sweden) and used in combination with a flow module, which had a volume of 40 μL for the interaction between the analyte and the substrate. The values relative to the surface coverage were extracted by using Sauerbrey's equation: $\Delta m = -C\Delta f/n$ where C is a constant relative to the sensor characteristics ($C=17.7$ $ng/(Hz \cdot cm^2)$), n is the odd overtone number (n=9 was taken for all the data presented) and $\Delta f$ is the frequency shift. The admissibility of the calculation of the adsorbed mass, as described above, is possible only when the sensor and layers above it are rigid. In numerical terms, the requirement is: $\Delta D/(\Delta f/i) < 0.4 \cdot 10^{-6}$ $Hz^{-1}$. This requirement was met throughout the experiments presented herein.

While specific embodiments and examples have been described herein in detail, those skilled in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. An affinity biosensor for sensing an analyte in a fluid, the biosensor comprising an interface for contacting the fluid and adsorption of the analyte, wherein the interface comprises a binary pattern of nanoscale regions having affinity for said analyte, the nanoscale regions isolated from one another by a passivated region in such a way that adsorption of said analyte on the interface is confined to said nanoscale regions, the nanoscale regions having diameters comprised in the range from 5 to 200 nm, the nanoscale regions together having a surface area amounting to at least 15% of the surface area of said interface, wherein the nanoscale regions have a surface functionalisation selective for the analyte.

2. The affinity biosensor as claimed in claim 1, wherein the nanoscale regions comprise nanodomes protruding from said passivated region.

3. The affinity biosensor as claimed in claim 1, wherein the nanodomes comprise a silica core.

4. The affinity biosensor as claimed in claim 1, wherein the nanoscale regions have an average diameter comprised in the range from 40 to 170 nm.

5. The affinity biosensor as claimed in claim 1, wherein the nanoscale regions are arranged in a hexagonal lattice.

6. An affinity biosensor for sensing an analyte in a fluid, the biosensor comprising an interface for contacting the fluid and adsorption of the analyte, wherein the interface comprises a binary pattern of nanoscale regions having affinity for said analyte, the nanoscale regions isolated from one another by a passivated region in such a way that adsorption of said analyte on the interface is confined to said nanoscale regions, the nanoscale regions having diameters comprised in the range from 5 to 200 nm, the nanoscale regions together having a surface area amounting to at least 15% of the surface area of said interface, wherein the nanoscale regions are arranged in a hexagonal lattice and wherein an average centre-to-centre distance between nearest-neighbour nanoscale regions amounts to between 1.5 and 5 times the average diameter of the nanoscale regions.

7. The affinity biosensor as claimed in claim 1, wherein the analyte includes a biomolecule, the surface functionalisation selective for the analyte affinity biosensor including, in said nanoscale regions, antibodies or receptors that the analyte can bind to.

8. An affinity biosensor for sensing an analyte in a fluid, the biosensor comprising an interface for contacting the fluid and adsorption of the analyte, wherein the interface comprises a binary pattern of nanoscale regions having affinity for said analyte, the nanoscale regions isolated from one another by a passivated region in such a way that adsorption of said analyte on the interface is confined to said nanoscale regions, the nanoscale regions having diameters comprised in the range from 5 to 200 nm, the nanoscale regions together having a surface area amounting to at least 15% of the surface area of said interface, wherein the passivated region comprises an anti-fouling layer.

9. The affinity sensor as claimed in claim 1, wherein the nanoscale regions together have a surface area amounting to at least 20% of the surface area of said interface.

10. A quartz crystal microbalance chip comprising an affinity biosensor for sensing an analyte in a fluid, the biosensor comprising an interface for contacting the fluid and adsorption of the analyte, wherein the interface comprises a binary pattern of nanoscale regions having affinity for said analyte, the nanoscale regions isolated from one another by a passivated region in such a way that adsorption of said analyte on the interface is confined to said nanoscale regions, the nanoscale regions having diameters comprised in the range from 5 to 200 nm, the nanoscale regions together having a surface area amounting to at least 15% of the surface area of said interface, the biosensor comprising a substrate contacted by electrodes for inducing therein shear deformations through the piezoelectric effect.

11. The quartz crystal microbalance chip of claim 10, comprising an affinity biosensor, wherein the nanoscale regions comprise nanodomes protruding from said passivated region, wherein the nanoscale regions have a surface functionalisation selective for the analyte, wherein the nanoscale regions have an average diameter comprised in the range from 40 to 170 nm, wherein the nanoscale regions are arranged in a hexagonal lattice, wherein an average centre-to-centre distance between nearest-neighbour nanoscale regions amounts to between 1.5 and 5 times the average diameter of the nanoscale regions, wherein the analyte includes a biomolecule, the affinity biosensor including, in said nanoscale regions, antibodies or receptors that the analyte can bind to, and wherein the passivated region comprises an anti-fouling layer.

12. A method of sensing an analyte in a fluid to be analysed, comprising: providing a quartz crystal microbalance chip, the quartz crystal microbalance chip comprising an affinity biosensor for sensing an analyte in a fluid, the biosensor comprising an interface for contacting the fluid and adsorption of the analyte, wherein the interface comprises a binary pattern of nanoscale regions having affinity for said analyte, the nanoscale regions isolated from one another by a passivated region in such a way that adsorption of said analyte on the interface is confined to said nanoscale regions, the nanoscale regions having diameters comprised in the range from 5 to 200 nm, the nanoscale regions together having a surface area amounting to at least 15% of the surface area of said interface, the biosensor comprising a substrate contacted by electrodes for inducing therein shear deformations through the piezoelectric effect;

contacting the interface with the fluid to be analysed, thereby allowing adsorption of the analyte on the interface, the adsorption being confined to said nanoscale regions;

determining an amount of adsorbed analyte.

13. The method as claimed in claim 12, comprising rinsing the interface after the interface has been contacted with the fluid to be analysed and wherein the amount of adsorbed analyte is determined after the rinsing.

14. The method as claimed in claim 12, wherein the ratio of the size of the average diameter of the nanoscale regions to the size of the analyte is situated in the range from 3 to 20.

15. An affinity biosensor for sensing an analyte in a fluid as claimed in claim 1, wherein the nanoscale regions comprise nanodomes protruding from said passivated region, wherein the nanoscale regions have an average diameter comprised in the range from 40 to 170 nm, wherein the nanoscale regions are arranged in a hexagonal lattice, wherein an average centre-to-centre distance between nearest-neighbour nanoscale regions amounts to between 1.5 and 5 times the average diameter of the nanoscale regions, wherein the analyte includes a biomolecule, the affinity biosensor including, in said nanoscale regions, antibodies or receptors that the analyte can bind to, and wherein the passivated region comprises an anti-fouling layer.

16. The affinity biosensor as claimed in claim 7, wherein the biomolecule includes at least one of protein, a carbohydrate, a lipid and a nucleic acid.

17. The affinity biosensor as claimed in claim 9, wherein the nanoscale regions together have a surface area amounting to at least 25% of the surface area of said interface.

18. The affinity biosensor as claimed in claim 9, wherein the nanoscale regions together have a surface area amounting to at least 30% of the surface area of said interface.

19. The quartz crystal microbalance chip of claim 10, comprising an affinity biosensor, wherein the nanoscale regions comprise nanodomes protruding from said passivated region, and wherein the nanoscale regions have a surface functionalisation selective for the analyte.

20. The quartz crystal microbalance chip of claim 19, wherein the analyte includes a biomolecule, the surface functionalisation selective for the analyte including, in said nanoscale regions, antibodies or receptors that the analyte can bind to, and wherein the passivated region comprises an anti-fouling layer.

21. The quartz crystal microbalance chip of claim 10, wherein the nanoscale regions have an average diameter comprised in the range from 40 to 170 nm.

22. The quartz crystal microbalance chip of claim 10, wherein the nanoscale regions are arranged in a hexagonal lattice, wherein an average centre-to-centre distance between nearest-neighbour nanoscale regions amounts to between 1.5 and 5 times the average diameter of the nanoscale regions.

\* \* \* \* \*